US00PP12536P2

(12) United States Plant Patent
Trees

(10) Patent No.: US PP12,536 P2
(45) Date of Patent: Apr. 9, 2002

(54) INTERSPECIFIC LOBELIA PLANT NAMED 'PERIWINKLE BLUE'

(76) Inventor: Scott Trees, 142 Seaview, Shell Beach, CA (US) 93449

( * ) Notice: Subject to any disclaimer, the term of this patent is extended or adjusted under 35 U.S.C. 154(b) by 0 days.

(21) Appl. No.: 09/535,886

(22) Filed: Mar. 27, 2000

(51) Int. Cl.[7] ..... A01H 5/00
(52) U.S. Cl. ..... Plt./263
(58) Field of Search ..... Plt./263

(56) References Cited

U.S. PATENT DOCUMENTS

PP10,758 P * 1/1999 Westhoff ..... Plt./263

* cited by examiner

*Primary Examiner*—Bruce R. Campell
*Assistant Examiner*—Wendy C Baker
(74) *Attorney, Agent, or Firm*—Gardner, Carton & Douglas

(57) ABSTRACT

A new and distinct Lobelia plant named 'Periwinkle Blue' is provided. This new cultivar was the result of a unique interspecific cross between *Lobelia erinus* and *Lobelia valida*. More specifically, the female or seed parent of 'Periwinkle Blue' was the *Lobelia erinus* Palace Series Blue With Eye and the male or pollen parent was an unnamed *Lobelia valida* plant.

1 Drawing Sheet

BACKGROUND OF THE INVENTION

The present invention comprises a new and distinctive Lobelia plant, hereinafter referred to by the cultivar name Periwinkle Blue. This new cultivar was the result of a unique interspecific cross between *Lobelia erinus* and *Lobelia valida*. More specifically, the breeding program which resulted in the production of the new cultivar was carried out at Arroyo Grande, Calif. in 1997. The female or seed parent of Periwinkle Blue was the *Lobelia erinus* plant from the Palace Series named 'Blue With Eye' (unpatented) which exhibits dark purple-blue flowers with white centers or "eyes" and has a semi-trailing habit. The male or pollen parent of Periwinkle Blue was an unnamed *Lobelia valida* plant which exhibits lavender-blue flowers and an upright habit. The resulting seed was collected and germinated. From the flowering progeny, a single plant was selected and initially designated BPF-100, and now given the cultivar name 'Periwinkle Blue'. The parentage of the new cultivar can be summarized as follows:

*Lobelia erinus*×*Lobelia valida*

Asexual reproduction of the new cultivar by terminal cuttings taken during 1998 and 1999 at Arroyo Grande, Calif., U.S.A. has demonstrated that the characteristics of the new cultivar as herein described are firmly fixed and are retained through successive generations of such asexual propagation.

SUMMARY OF INVENTION

It was found that the cultivar of the present invention:

(a) exhibits initial upright growth followed by a semi-trailing habit, (b) forms sky-blue flowers with white "eyes", (c) exhibits a vigorous growth habit, (d) is extremely floriferous.

The 'Periwinkle Blue' cultivar has not been observed under all possible environmental conditions to date. Accordingly, it is possible that the phenotype may vary somewhat with variations in the environment, such as temperature, light intensity, and day length.

When the new cultivar of the present invention is compared to the Lobelia plant 'Azuro' (U.S. Plant Pat. No. 10,758) it is found that the new cultivar exhibits a more vigorous, trailing growth habit and lighter blue flower color.

BRIEF DESCRIPTION OF THE PHOTOGRAPH

The accompanying photographs show as nearly true as it is reasonably possible to make the same in color illustrations of this type, typical flower and foliage characteristics of the new cultivar. The plants were grown in a greenhouse at West Chicago, Ill., USA.

DETAILED BOTANICAL DESCRIPTION

The chart used in the identification of colors described herein is The R.H.S. Colour Chart of The Royal Horticultural Society, London, England. The color values were determined on Mar. 13, 2000 in West Chicago, Ill. The readings were taken between 1:00 and 1:45 p.m. under approximately 2500 footcandles of light. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night. The plants used for the following descriptions and measurements were grown for 9 weeks after the planting of rooted cuttings.

Commercial classification: Trailing Interspecific Lobelia hybrid.

Propagation:

*Type cutting.*—Terminal tip.

*Time to initiate roots.*—Approximately 14–21 days with the shorter times generally being experienced in the summer and the longer times in the winter.

*Root description.*—Fibrous.

*Crop time.*—Finished plants are produced eight to ten weeks after planting of rooted cuttings in 10 cm pots.

Plant description:

*General appearance and form.*—Upright to trailing.

*Plant height.*—Approximately 21 cm.

*Plant width.*—Approximately 30 cm.

*Branching habit.*—Freely branching with lateral branches forming at every node.

*Lateral branch diameter.*—Approximately 2 mm.

*Internode length.*—Approximately 3.3 cm.

*Stem color.*—Yellow-Green Group 137A.

*Stem texture.*—Smooth.

Foliage description:

*Leaf form.*—Single, simple.

*Leaf arrangement.*—Alternate.

*Leaf texture.*—Smooth.

*Leaf base.*—Attenuate, sessile.

*Leaf aspect.*—Flat.

*Upper leaves.*—Shape: linear. Margin: remotely serrate. Apex: acute. Size: 2.7 cm in length, 0.5 cm in width. Color of mature foliage: upper surface — 137A, lower surface — 137B.

*Lower leaves.*—Shape: Spatulate/obovate. Margin: closely serrate. Apex: rounded. Size: 5 cm in length, 1.3 cm in width. Color of mature foliage: upper surface — 137B, lower surface — 137C.

Flower description:

*Flowering habit.*—Periwinkle Blue is freely flowering under outdoor growing conditions with substantially continuous blooming from spring until fall.

*Flowers borne.*—Outwardly, inverted because of twisted pedicel.

*Pedicel length.*—Approximately 2 cm.

*Pedicel color.*—141B.

*Flower form.*—Labiate, upper lip consists of two small petals; lower lip consists of three broader petals. Petals are fused at base forming a tube, tube is split almost to base along one side.

*Flower arrangement.*—Singly, in loose racemes.

*Quantity of flowers.*—Numerous, one per axil.

*Flower size.*—Diameter: approximately 1.6 cm, length: approximately 1.8 cm.

*Petal texture.*—Smooth, dull.

*Petal margin.*—Entire.

*Upper petals.*—Shape: linear, size: 8 mm in length, 3 mm in width at tip.

*Lower petals.*—Shape: Obovate, size: 1 cm in length, 6 mm in width at tip.

*Flower color.*—Upper surface of upper petals is 99C, lower surface of upper petals is 96C. Middle lower petal is white from throat ⅔ of the way to margin, 95C marginal ⅓. Side lower petals are 99C along the outer, lateral ½ and marginal ⅓, RHS 155D on inner ½ for ⅔ the distance from throat to margin. The three lower petals are fused for ½ of their length. Yellow spots (between 154A and 1A) appear at base where petals are joined, streaks of 101A appear at base along division of areas of white and 99C. All petals fade to 95C.

*Flower bud shape.*—Tubular.

*Flower bud length.*—Approximately 1.1 cm.

*Flower bud diameter.*—Approximately 3 mm.

*Sepals.*—Five, fused to form calyx.

*Calyx.*—Length: approximately 8 mm, diameter: approximately 2 mm, apex: acuminate, texture: smooth, color: 137C.

*Reproductive organs.*—Stamens: quantity — 5, approximately 8 mm in length, filament color — 100D, anther length — approximately 2 mm, anther color — 103B. Pistil: approximately 9 mm in length, the stigma is round, its color is 89A, the style color is 144A, the ovary color is 144A.

*Disease resistance.*—Resistance to pathogens has not been observed.

*Seed production.*—Seed production has not been observed.

What is claimed is:

1. A new and distinct Lobelia plant named 'Periwinkle Blue' substantially herein illustrated and described, which:

a) Exhibits initial upright growth followed by a semi-trailing habit, (b) Forms sky-blue flowers with white 'eyes', (c) Exhibits a vigorous growth habit, (d) Is extremely floriferous.

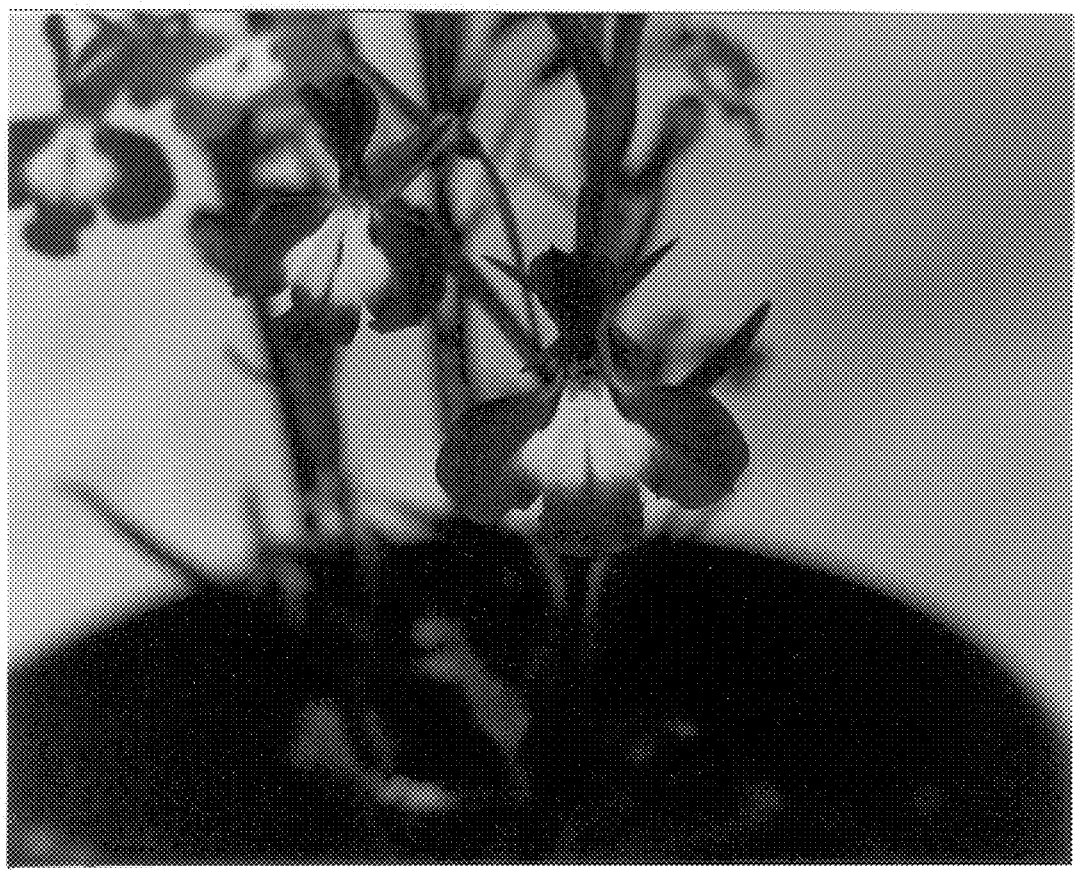

* * * * *